(12) United States Patent
Fischer et al.

(10) Patent No.: US 6,452,053 B2
(45) Date of Patent: *Sep. 17, 2002

(54) BLEACHING-ACTIVE DENDRIMER LIGANDS AND METAL COMPLEXES THEREOF

(75) Inventors: Claudia Fischer, Eschborn; Jörg Issberner, Krefeld; Fritz Vögtle, Alfter-Impekoven, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/839,730

(22) Filed: Apr. 20, 2001

(30) Foreign Application Priority Data

Apr. 20, 2000 (DE) .......................................... 100 19 878

(51) Int. Cl.$^7$ ............................................ C07C 211/00
(52) U.S. Cl. .................... 564/307; 564/463; 556/45; 556/136; 556/137; 502/200; 502/204; 510/376; 510/499
(58) Field of Search ................ 564/307, 463; 556/45, 136, 137; 510/303, 311, 312, 372, 376, 499; 502/200, 204

(56) References Cited

U.S. PATENT DOCUMENTS

| 2,928,876 A | 3/1960 | Spivack et al. ............. 260/566 |
| 5,847,190 A | 12/1998 | Paulus et al. ............... 558/302 |

FOREIGN PATENT DOCUMENTS

| DE | 196 21 510 | 12/1997 |
| DE | 198 09 713 | 7/1999 |
| EP | 0 458 397 | 11/1991 |
| JP | 11-50096 | 2/1999 |
| WO | WO 96/06154 | 2/1996 |
| WO | WO 01/05925 | 1/2001 |

OTHER PUBLICATIONS

English Translation of the Abstract of DE 198 09 713.
English Translation of the Abstract of DE 196 21 510.
R. Moors, F. Vogtle, Dendrimere Polyamine, Chem. Ber. 1993, 126, pp. 2133–2135, 1993.
EPO Search Report for Application No. 01109628, Mail Date of Aug. 29, 2001.
English Abstract Translation for JP 11–50096.
Naohide Matsumoto, et al., "Synthesis and Characterization of a Chloro–bridged Binuclear Iron (III) Complex," Bull. Chem. Soc. Jpn., No. 58, pp. 3621–3622.
Jorg Issberner, et al., "Poly(Amine/imine) Dendrimers Bearings Planar Chiral Terminal Groups—Synthesis and Chiroptical Properties," Tetrahedron: Asymmetry, Elsevier Scient Ltd. (Great Britain), vol. 7 (No. 8), pp. 2223–2232.
Joaquin Barbera, et al., "Copper–containing dendromesogens: the influence of the metal on the mesomorphism," Liquid Crystals, Taylor and Francis Ltd., vol. 27 (No. 2), pp. 225–262.
See IDS Filed on Jul. 30, 2001 for R. Moors, F. Vogtle, Dendrimere Polyamine, Chem. Ber. 1993, 126, pp. 2133–2135, 1993.

Primary Examiner—Gregory DelCotto
(74) Attorney, Agent, or Firm—Richard P. Silverman

(57) ABSTRACT

Compounds of the formula $$(R^1R^1)N\text{—}X\text{—}N(R^1R^1) \qquad (I)$$

are claimed, where $R^1$ and X have the meanings given in the description.

5 Claims, No Drawings

BLEACHING-ACTIVE DENDRIMER LIGANDS AND METAL COMPLEXES THEREOF

BACKGROUND OF THE INVENTION

It is known that the bleaching power of peroxide bleaches, such as hydrogen peroxide, perborates, percarbonates, persilicates and perphosphates, in laundry detergents and cleaners, and thus the efficiency of these bleaches for the removal of tea, coffee, fruit or red wine stains only fully develops at relatively high temperatures of significantly more than 60° C. To improve the bleaching action, which is greatly reduced at relatively low temperatures, below 60° C. in particular, it is possible to use compounds to activate the peroxide bleaches. A number of transition metal salts and corresponding complexes with mostly chelating compounds have been proposed for this purpose, although the effectiveness of a metal or of a specific combination of transition metal and complex ligand cannot be predicted.

A large number of specifications, for example WO 96/06154 and EP 458 397, claim metal complexes with a high activation potential. DE 1 980 9713 describes transition metal complexes with polyamidoamine dendrimer ligand systems. It is an object to find bleaching catalysts which have a high oxidizing and bleaching capacity and which also harm the colors of dyed textiles or surfaces, and the textile fibers as little as possible.

A dendritic polyamine and its cobalt complex are described in Chem. Ber. 1993, pp. 2133–2135. DE-A-196 21510 describes dendrimers with planar-chiral or axial-chiral end groups.

SUMMARY OF THE INVENTION

We have now found that transition metal complexes with dendrimers of the polyalkyleneimine type improve the bleaching action of peroxygen compounds during the bleaching of colored soilings both on textiles and on hard surfaces, without harming colors and fibers. Moreover, we have found that the use of dendrimers which are not bonded to form complexes with transition metals in laundry detergents and cleaners enhance the oxidizing and bleaching capacity of the compositions in aqueous solution.

The invention provides compounds of the formula $$(R^1R^1)N—X—N(R^1R^1) \qquad (I)$$

in which $R^1$ is a group of the formula $(R^2R^3)N—(CH_2)_n—$, $R^2$ and $R^3$ are in each case a group of the formula $(R^4R^5)N—(CH_2)_n—$, n is the numbers 2 or 3, or $R^2$ and $R^3$ together are the group of the formula A or $R^2$ is hydrogen and $R^3$ is a group of the formula

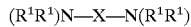
—COCHCH$_2$NA,
      |
      NA $R^4$ and $R^5$ are in each case a group of the formula $(R^6R^7)—N—(CH_2)_n—$, n is the numbers 2 or 3, or $R^4$ and $R^5$ together are the group of the formula A or $R^4$ is hydrogen and $R^5$ is a group of the formula

—COCHCH$_2$NA,
      |
      NA $R^6$ and $R^7$ are in each case a group of the formula $(R^8R^9)N—(CH_2)_n—$, n is the numbers 2 or 3, or $R^6$ and $R^7$ together are the group of the formula A or $R^6$ is hydrogen and $R^7$ is a group of the formula

—COCHCH$_2$NA,
      |
      NA $R^8$ and $R^9$ together are the group of the formula A or $R^8$ is hydrogen and $R^9$ is a group of the formula

—COCHCH$_2$NA,
      |
      NA

A is a group of the formula

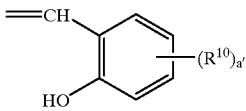

in which a is an integer from 1 to 4, and $R^{10}$ is hydrogen, $C_{1-30}$-alkyl, cycloalkyl or aryl radicals, $C_{1-4}$-alkoxy groups, substituted or unsubstituted amino or ammonium groups, halogen atoms, sulfo groups, carboxyl groups or groups of the formula —(CH$_2$)$_r$—COOH, —(CH$_2$)$_r$—SO$_3$H, —(CH$_2$)$_r$—PO$_3$H$_2$, —(CH$_2$)$_r$—OH, where r is an integer from 0 to 4, and said acid groups may also be present in salt form, and X is a group of the formulae
—(CH$_2$)$_n$—, —(CH$_2$)$_3$—NR$^{11}$—(CH$_2$)$_3$—, —(CH$_2$)$_2$—NR$^{11}$—(CH$_2$)$_2$—, $C_2$–$C_{20}$-alkylene, —(CH$_2$)$_l$—[O—(CH$_2$)$_k$]$_m$—O—CH$_2$)$_l$)—, n is a number from 2 to 20, l and k are a number from 2 to 6, m is a number from 1 to 40, [lacuna] $C_1$–$C_{20}$-alkyl, $C_2$–$C_{20}$-dialkylamino-$C_2$–$C_{10}$-alkyl, $C_1$–$C_{10}$-alkoxy-$C_2$–$C_{10}$-alkyl, $C_4$–$C_{30}$-dialkylamino-alkenyl, $C_3$–$C_{30}$-alkoxyalkenyl, $C_3$–$C_{20}$-hydroxyalkenyl, $C_5$–$C_{20}$-cycloalkyl-alkenyl, optionally by $C_1$–$C_8$-alkyl, $C_2$–$C_8$-dialkylamino, $C_1$–$C_8$-alkoxy, hydroxyl, $C_3$–$C_8$-cycloalkyl, $C_4$–$C_{12}$-cycloalkyl-alkyl, or together are an alkylene chain optionally interrupted by nitrogen or oxygen, such as ethylene oxide, propylene oxide, butylene oxide or —CH$_2$—CH(CH$_3$)—O—.

The invention further provides complexes of the above-defined compounds with cobalt, manganese, iron, ruthenium, vanadium, molybdenum or tungsten. Preference is given to manganese complexes. These compounds and the corresponding metal complexes are suitable as bleaching and oxidation catalysts in the case of peroxygen compounds, in particular in laundry detergents and cleaners which comprise peroxygen compounds, for example universal laundry detergents or machine dishwashing detergents. These catalysts improve the oxidizing and bleaching action of the inorganic peroxygen compounds at temperatures below 80° C., in particular in the temperature range from 15 to 45° C. with simultaneous reduction in color and textile fiber damage. Moreover, the compounds defined above and metal complexes thereof can also be used in the bleaching of paper.

The preparation of the polysalene dendrimers of the formula I has been carried out by a method described in the specialist literature (R. Moors, F. Vögtle, Chem. Ber. 1993, 126, 2133–2135). The initiator core used here is ethylenediamine, which is converted by a Michael Addition with acrylonitrile. The terminal nitrile groups are reduced to give the amine, as a result of which a further addition of acrylonitrile is made possible. By repeating this synthesis frequency, the number of functionalities doubles. In each of these synthesis stages, the amino groups can be reacted with salicylaldehyde, giving compounds of the formula I containing the group A. Reaction of the amino groups with ∀,∃-diaminopropionic acid and subsequent reaction with salicylaldehyde gives compounds of the formula I which contain groups of the formula —COCHNA—CH$_2$NA.

The products are formed as yellow solids or oils.

The complexation with metal cations can take place in three different ways. In the first method, the ligand is prepared as described by Moors and Vögtle. This is then followed, in a suitable solvent, e.g. chloroform, methylene chloride, ethanol, methanol, dimethylformamide, water, dimethyl sulfoxide or mixtures thereof, by the reaction with the metal cation, for example to give the dendritic complex.

In a second embodiment, salicylaldehyde, dendritic polyamine and metal salt are combined in a one-pot reaction in a suitable solvent, e.g. chloroform, methylene chloride, ethanol, methanol, dimethylformamide, water, dimethyl sulfoxide or mixtures thereof, forming the catalysts according to the invention. In the third embodiment, the metal-free polysalene dendrimer can be used. In this case, the dendrimer takes up the metal cations present in the water during use and acts as catalyst. It is also possible to use the metal-free polysalene dendrimer, optionally incorporated into a matrix, and a suitable metal salt separately in a laundry detergent formulation. By dissolving the laundry detergent formulation, the reactants are able to meet and form the catalyst.

Preference is given to the compounds of the formula I which contain groups A. Particular preference is given to the compounds and the metal complexes thereof 4-cascade:ethylenediamine [4]:(1-azabutylidene):2-methinephenol, 8- cascade:ethylenediamine[4]:(1-azabutylidene)$^2$:2- methinephenol, 16-cascade:ethylenediamine[4]:(1-azabutylidene)$^3$:2-methinephenol, 32-cascade:ethylenediamine[4]:(1-azabutylidene)$^4$:2-methinephenol.

Where appropriate, the dendrimer nomenclature proposed by Newkome has been used for dendritic compounds [G. R. Newkome, C. Morefield, F. Vögtle in Dendritic Macromolecules, VCH, Weinheim 1996].

Such dendrimers can be loaded with stoichiometrically different amounts of transition metal. In the maximum case, all nitrogen atoms of the dendrimer are saturated with transition metal.

In addition to the peripheral N atoms, internal nitrogen atoms of the dendrimer can also form complexes, and the resulting complex can have a catalytic action. The total number of peripheral and internal nitrogen atoms are:

| Generation: | 0 | 1 | 2 | 3 | 4 | 5 | ... |
|---|---|---|---|---|---|---|---|
| Number of N atoms: | 2 | 6 | 14 | 30 | 62 | 126 | |

The transition metals in the complexes to be used according to the invention can have oxidation states in the range from +II to +V, depending on the metal. Manganese, cobalt and molybdenum are the preferred transition metals. Polynuclear systems with mixed oxidation numbers and/or two or more different transition metals are also possible.

Apart from the dendrimer ligand, the complex compounds to be used according to the invention can also carry further ligands which usually have a simpler structure, in particular neutral or mono- or polyvalent anionic ligands. Suitable ligands are, for example, water, nitrate, acetate, formate, citrate, perchlorate and the halides, such as chloride, bromide and iodide, and complex anions, such as hexafluorophosphate. The anionic ligands serve to balance the charge between transition metal center and the ligand system. The presence of oxo ligands, peroxo ligands and imino ligands is also possible. These additional ligands can also act as bridges, meaning that oligomeric polynuclear complexes with at least one dendrimer ligand arise.

The transition metal dendrimer complexes according to the invention, but also the dendrimers as such are highly suitable as bleaching and oxidation catalysts, in particular in laundry detergent and cleaners for the cleaning of textiles and also of hard surfaces, in particular of dishes, and in the bleaching of textiles and paper.

The laundry detergent and cleaners comprise these bleach catalysts in the amounts by weight of from 0.0001 to 0.5% by weight, in particular 0.00025 to 0.25% by weight, especially 0.0005 to 0.1% by weight, based on the weight of the formulations.

EXAMPLES

The examples below serve to illustrate the invention in more detail without limiting it thereto.

Example 1

[4-Cascade:ethylenediamine [4]:(1-azabutylidene):2-methinephenol] manganese 5.16 g (43 mmol) of salicylaldehyde were dissolved in a suspension of 100 ml of toluene and 30 g of Na$_2$SO$_4$. Over a period of 1 h, 3.05 g (10.6 mmol) of 4-cascade:ethylenediamine [4]:3-propylamine suspended beforehand in toluene were added dropwise thereto. The mixture was stirred for a further 24 h at room temperature and then filtered. The solvent was removed under reduced pressure.

1.3 g of the resulting compound (1.84 mmol) were refluxed with 900 mg (3.67 mmol) of manganese diacetate in 50 ml of ethanol for 6 h. The reaction solution was then concentrated by evaporation to about 15 ml, left to stand overnight in a refrigerator, the solvent was completely removed and the residue was taken up with about 10 ml of MeOH. The complex crystallized out of the solution as a brown solid (yield: 1.8 g).

Example 2

[8-Cascade:ethylenediamine [4]:(1-azabutylidene)$^2$:2-methinephenol] manganese 2.2 g (18 mmol) of salicyl aldehyde were dissolved in a suspension of 50 ml of toluene and 15 g of Na$_2$SO$_4$. Over a period of 1 h, 1.53 g (2.05 mmol) of the octamine (CH$_2$N (CH$_2$CH$_2$N(CH$_2$CH$_2$NH$_2$)$_2$)$_2$)$_2$ suspended beforehand in 50 ml of toluene were added dropwise thereto, and the solution turned yellow. The mixture was stirred for a further 24 h at room temperature and then filtered. The solvent was removed under reduced pressure and the high-viscosity yellow residue was washed repeatedly with hot methanol.

2.93 g of the resulting compound (1.86 mmol) in 150 ml of ethanol were firstly treated with 30 ml of 0.5 m KOH and refluxed for 30 min. Manganese diacetate (4.6 g, 18.77 mmol) was then added, and the mixture was refluxed for 45 min and cooled. Following the addition of 0.95 g of LiCl in 7.5 ml of water, the mixture is stirred for a further 45 min at room temperature. The complex crystallizes out of the solution as a brown solid (yield: 3.8 g).

What is claimed is:

1. A compound having the formula I $$(R^1R^1)N-X-N(R^1R^1) \quad (I)$$

or metal complexes thereof with transition metals, in which $R^1$ is a group of the formula $(R^2R^3)N-(CH_2)_n-$, $R^2$ and $R^3$ are in each case a group of the formula $(R^4R^5)N-(CH_2)_n-$, n is the numbers 2 or 3, or $R^2$ is hydrogen and $R^3$ is a group of the formula

—COCHCH₂NA,
      |
      NA $R^4$ and $R^5$ are in each case a group of the formula $(R^6R^7)-N-(CH_2)_n-$, n is the numbers 2 or 3, or $R^4$ and $R^5$ together are the group of the formula A or $R^4$ is hydrogen and $R^5$ is a group of the formula

—COCHCH₂NA,
      |
      NA $R^6$ and $R^7$ are in each case a group of the formula $(R^8R^9)N-(CH_2)_n-$, n is the numbers 2 or 3, or $R^6$ and $R^7$ together are the group of the formula A or $R^6$ is hydrogen and $R^7$ is a group of the formula

—COCHCH₂NA,
      |
      NA $R^8$ and $R^9$ together are the group of the formula A or $R^8$ is hydrogen and $R^9$ is a group of the formula

—COCHCH₂NA,
      |
      NA

A is a group of the formula

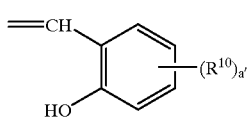

in which a is an integer from 1 to 4, and $R^{10}$ is hydrogen, $C_1$–$C_{30}$-alkyl, $C_1$–$C_4$-alkoxy groups, substituted or unsubstituted amino or ammonium groups, halogen atoms, sulfo groups, carboxyl groups or groups of the formula $-(CH_2)_r-COOH$, $-(CH_2)_r-SO_3H$, $-(CH_2)_r-PO_3H_2$, $-(CH_2)_r-OH$, where r is an integer from 0 to 4, and said acid groups may also be present in salt form, and X is a group of the formulae $-(CH_2)_n-$, $-(CH_2)_3-NR^{11}-(CH_2)_3-$, $-(CH_2)_2-NR^{11}-(CH_2)_2-$, $C_2$–$C_{20}$-alkylene, $-(CH_2)_l-(O-(CH_2)_k)_m-O-CH_2)_l-$, n is a number from 2 to 20, l and k are a number from 2 to 6, m is a number from 1 to 40, $R^{11}$ is $C_1$–$C_{20}$-alkyl, $C_2$–$C_{20}$-dialkylamino-$C_2$–$C_{10}$-alkyl, $C_1$–$C_{10}$-alkoxy-$C_2$–$C_{10}$-alkyl, $C_2$–$C_{20}$-hydroxyalkyl, $C_3$–$C_{12}$-cycloalkyl, $C_4$–$C_{20}$-cycloalkyl-alkyl, $C_2$–$C_{20}$-alkenyl, $C_4$–$C_{30}$-dialkylamino-alkenyl, $C_3$–$C_{30}$-alkoxyalkenyl, $C_3$–$C_{20}$-hydroxyalkenyl, $C_5$–$C_{20}$-cycloalkyl-alkenyl, aryl or $C_7$–$C_{20}$-aralkyl, which are unsubstituted or substituted by $C_1$–$C_8$-alkyl, $C_2$–$C_8$-dialkylamino, $C_1$–$C_6$, alkoxy, hydroxy, $C_3$–$C_8$-cycloalkyl, $C_4$–$C_{12}$-cycloalkylalkyl, or two of these substitutents may form together an alkylene chain optionally interrupted by nitrogen or oxygen.

2. A complex of the compound of the formula I as claimed in claim 1 with Co, Mn, Fe, Ru, V, Mo or W.

3. A complex of the compound of the formula I as claimed in claim 1 with Mn.

4. A compound of the formula I as claimed in claim 1, where X is a group of the formula $-(CH_2)_n-$ and n is a number from 2 to 20.

5. The compound of claim 1 wherein, with respect to R11, the alkylene chain optionally interrupted by nitrogen or oxygen is selected from the group consisting of ethylene oxide, propylene oxide, butylene oxide, and $-CH_2CH(CH_3)-O-$.

* * * * *